US008906937B2

(12) United States Patent
Padmanabhan et al.

(10) Patent No.: US 8,906,937 B2

(45) Date of Patent: Dec. 9, 2014

(54) FLAVIVIRUS INHIBITORS AND METHODS OF THEIR USE

(71) Applicants: Radhakrishnan Padmanabhan, Bethesda, MD (US); Nagarajan Pattabiraman, North Potomac, MD (US); Niklaus Mueller, Denver, CO (US); Kuppuswamy Nagarajan, Bangalore (IN)

(72) Inventors: Radhakrishnan Padmanabhan, Bethesda, MD (US); Nagarajan Pattabiraman, North Potomac, MD (US); Niklaus Mueller, Denver, CO (US); Kuppuswamy Nagarajan, Bangalore (IN)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/033,086

(22) Filed: Sep. 20, 2013

(65) Prior Publication Data

US 2014/0038962 A1 Feb. 6, 2014

Related U.S. Application Data

(63) Continuation of application No. 13/120,583, filed as application No. PCT/US2009/058048 on Sep. 23, 2009, now Pat. No. 8,563,580.

(60) Provisional application No. 61/099,411, filed on Sep. 23, 2008.

(51) Int. Cl.

| | |
|---|---|
| ***A61K 31/47*** | (2006.01) |
| ***C07D 215/00*** | (2006.01) |
| ***C07D 401/12*** | (2006.01) |
| ***C07D 277/36*** | (2006.01) |
| ***C07D 413/12*** | (2006.01) |
| ***C07D 417/12*** | (2006.01) |
| ***C07D 417/06*** | (2006.01) |
| ***C07D 405/14*** | (2006.01) |
| ***C07D 215/26*** | (2006.01) |
| ***C07D 409/06*** | (2006.01) |
| ***A61K 31/4709*** | (2006.01) |

(52) U.S. Cl.

CPC ............ *C07D 277/36* (2013.01); *C07D 401/12* (2013.01); *C07D 413/12* (2013.01); *C07D 417/12* (2013.01); *C07D 417/06* (2013.01); *C07D 405/14* (2013.01); *C07D 215/26* (2013.01); *C07D 409/06* (2013.01); *A61K 31/4709* (2013.01)

USPC .......................................... 514/314; 546/177

(58) Field of Classification Search

USPC .......................................... 546/177; 514/314

See application file for complete search history.

(56) References Cited

U.S. PATENT DOCUMENTS

| | | | |
|---|---|---|---|
| 5,698,579 | A | 12/1997 | Muller |
| 6,495,358 | B1 | 12/2002 | Groutas |
| 6,667,316 | B1 | 12/2003 | Man et al. |
| 8,119,656 | B2 | 2/2012 | Roth et al. |
| 8,563,580 | B2 | 10/2013 | Padmanabhan et al. |
| 2007/0027066 | A1 | 2/2007 | LaColla et al. |
| 2007/0219218 | A1 | 9/2007 | Yu et al. |

FOREIGN PATENT DOCUMENTS

| | | |
|---|---|---|
| WO | 0146183 | 6/2001 |
| WO | 02081463 | 10/2002 |
| WO | 2004058704 | 7/2004 |
| WO | 2005030727 | 4/2005 |
| WO | 2005037845 | 4/2005 |
| WO | 2006020879 | 2/2006 |
| WO | 2006091858 | 8/2006 |

OTHER PUBLICATIONS

Reference Method for Broth Dilution Antifungal Susceptibility Testing of Yeasts: Approved Standard—Third Edition. CLSI Document M27-A3, Clinical and Laboratory Standards Institute (CLSI) vol. 28, No. 14, 2008.

U.S. Appl. No. 13/120,583, Notice of Allowance mailed on Jul. 18, 2013, 10 pages.

U.S. Appl. No. 13/120,583, Office Action mailed on Jan. 4, 2013, 10 pages.

U.S. Appl. No. 13/120,583, Restriction Requirement mailed on Mar. 15, 2012, 10 pages.

U.S. Appl. No. 13/120,583, Restriction Requirement mailed on Mar. 29, 2012, 10 pages.

Allin et al., Neighboring Group Assistance in the Formation of Phthalimidines from o-Phthalaldehyde, Synlett, 1996, pp. 781-782.

Alvarez et al., A Practical Procedure for the Synthesis of Alkyl Azides at Ambient Temperature in Dimethyl Sulfoxide in High Purity and Yield, Synthesis, 1997, pp. 413-414.

Amyes et al., Rational Design of Transition-state Analogues as Potent Enzyme Inhibitors with Therapeutic Potential, ACS Chem. Biol., vol. 2, 2007, pp. 711-714.

Armstrong et al., The Prevalence of Hepatitis C Virus Infection in the United States, 1999 through 2002, Ann. Intern. Med., vol. 144, 2006, pp. 705-714.

Bartenschlager et al., Non-structural Protein 3 of the Hepatitis C Virus Encodes a Serine-type Proteinase Required for Cleavage at the NS3/4 and NS4/5 Junctions, J Virol., vol. 67, 1993, pp. 3835-3844.

(Continued)

*Primary Examiner* — Samantha Shterengarts

(74) *Attorney, Agent, or Firm* — Kilpatrick Townsend & Stockton, LLP

(57) ABSTRACT

Methods of treating, preventing, and/or ameliorating a *Flavivirus* infection in a subject are disclosed. The methods comprise administering to the subject a therapeutically effective amount of a *Flavivirus* inhibitor, e.g., a *Flavivirus* serine protease inhibitor. These methods are useful in treating, preventing, and/or ameliorating *Flavivirus* infections such as, for example, West Nile Virus, Dengue Virus, and Japanese Encephalitis Virus.

7 Claims, 2 Drawing Sheets

(56) References Cited

OTHER PUBLICATIONS

Bartenschlager et al., Replication of the Hepatitis C Virus in Cell Culture, Antiviral Res., vol. 60, 2003, pp. 91-102.
Bartenschlager, The NS3/4A Proteinase of the Hepatitis C Virus: Unravelling Structure and Function of an Unusual Enzyme and a Prime Target for Antiviral Therapy, J Virol Hepatitis, vol. 6, 1999, pp. 165-181.
Beaulieu, Non-nucleoside Inhibitors of the HCV NS5B Polymerase: Progress in the Discovery and Development of Novel Agents for the Treatment of HCV Infections, Curr. Opin. Investigat. Drugs, vol. 8, 2007, pp. 614-634.
Behrens et al., Identification and Properties of the RNA-Dependent RNA Polymerase of Hepatitis C Virus, Embo. J, vol. 15, 1996, pp. 12-22.
Beran et al., The Serine Protease Domain of Hepatitis C Viral NS3 Activates RNA Helicase Activity by Promoting the Binding of RNA Substrate, J Biol. Chem., vol. 282, 2007, pp. 34913-34920.
Blagg, Structure-Activity Relationships for In Vitro and In Vivo Toxicity, Ann. Rev. Med. Chem., vol. 41, 2006, pp. 353-368.
Bleicher, Hit and Lead generation: Beyond High-throughput Screening, Nat. Rev. Drug Discov., vol. 2, 2003, pp. 369-378.
Blight et al., Efficient Initiation of HCV RNA Replication in Cell Culture, Science, vol. 290, 2000, pp. 1972-1974.
Blight et al., Efficient Replication of Hepatitis C Virus Genotype 1a RNAs in Cell Culture, J Virol. , vol. 77, 2003, pp. 3181-3190.
Bohm et al., Scaffold Hopping, Drug Discov. Today-Technologies vol. 1, 2008, pp. 217-224.
Breinbauer et al., Azide-Aikyne Coupling: A Powerful Reaction for Bioconjugate Chemistry, ChemBioChem, vol. 4, 2003, pp. 1147-1149.
Brown et al., Secondary Structure of the 5' Nontranslaled Regions of Hepatitis C Virus and Pestivirus Genomic RNAs, Nucleic Acids Res., vol. 20, 1992, pp. 5041-5045.
Bukh et al., Sequence Analysis of the 5' Noncoding Region of Hepatitis C Virus, Proc. Nail Acad. Sci. USA vol. 89, 1992, pp. 4942-4946.
Chan et al., Identification of N,N-disubslituted Phenylalanines as a Novel Class of Inhibitors of Hepatitis C NS5B Polymerase, J Med Chem., vol. 46, 2003, pp. 1283-1285.
Chen et al., The Use of Bioisosteric Groups in Lead Optimization, Ann Rep Med Chem., vol. 38, 2003, pp. 333-346.
Crute et al., Herpes Simplex Virus Helicase-primase Inhibitors are Active in Animal Models of Human Disease, Nature Medicine vol. 8, 2002, pp. 386-391.
Del Vecchio et al., Small Molecule and Biologic Inhibitors of Hepatitis C Virus: A Symbiotic Approach, Mini-Reviews Med Chem., vol. 6, 2006, pp. 1263-1268.
Delaney, Esol: Estimating Aqueous Solubility Directly from Molecular Structure, J Chem. Inf. Comput. Sci. vol. 44, 2004, pp. 1000-1005.
Di et al., Profiling Drug-like Properties in Discovery Research, Curr. Opin. Chem. Biol., vol. 7, 2003, pp. 402-408.
Didziapetris et al., Classification Analysis of P-glycoprotein Substrate Specificity, J Drug Target, vol. 11, 2003, pp. 391-406.
Du et al., Establishment of a Simple Assay in vitro for Hepatitis C Virus NS3 Serine Protease Based on Recombinant Substrate and Single-chain Protease, World J Gastroenterol, vol. 8, 2002, pp. 1088-1093.
Dumont et al., RNA Translocation and Unwinding Mechanism of HCV NS3 Helicase and its Coordination by ATP, Nature, vol. 439, 2006, pp. 105-109.
Dunlop et al., Implementing hERG Screening Early in the Preclinical Drug Discovery Process, Amer. Drug Discov. vol. 1, 2006, pp. 8-13.
Ertl et al., Fast Calculation of Molecular Polar Surface Area as a Sum of Fragment-Based Contributions and its Application to the Prediction of Drug Transport Properties, J Med. Chem., vol. 43, 2000, pp. 3714-3717.
Fermini et al., Pre-Clinical Assessment of Drug-Induced QT Interval Prolongation. Current Issues and Impact on Drug Discovery, Ann. Rep. Med. Chem., vol. 39, 2004, pp. 323-334.
Frick, The Hepatitis C Virus NS3 Protein: a Model RNA Helicase and Potential Drug Target, Curr. Issues Mol. Biol., vol. 9, 2007, pp. 1-20.
Ganesh et al., Identification and Characterization of Nonsubstrate Based Inhibitors of the Essential Dengue and West Nile Virus Proteases, Bioorganic and Medicinal Chemistry, vol. 13 (1), 2005, pp. 257-264.
Garfunkle et al., Optimization of the Central Heterocycle of a-Ketoheterocycle Inhibitors of Fatty Acid Amide Hydrolase, J Med. Chem., vol. 51, 2008, pp. 4392-4403.
Gillespie et al., The Hit-to-Lead Process in Drug Discovery, Ann. Rep. Med. Chem., vol. 39, 2004, pp. 293-304.
Gopalsamy et al., Discovery of Pyrano[3,4-b]indoles as Potent and Selective HCV NS5B Polymerase Inhibitors, J Med. Chem., vol. 47, 2004, pp. 6603-6608.
Goudreau et al., The Therapeutic Potential of NS3 Protease Inhibitors in HCV Infection, Expert Opin. Investig. Drugs, vol. 14, 2005, pp. 1129-1144.
Groutas et al., Structure-Based Design of a General Class of Mechanism-Based Inhibitors of the Serine Proteases Employing a Novel Amino Acid-Derived Heterocyclic Scaffold, Biochemistry, vol. 36, 1997, pp. 4739-4750.
Guengerich, Cytochrome P450 and Chemical Toxicology, Chem. Res. Toxicol., vol. 21, 2008, pp. 70-83.
Harrison, Small Molecule and Novel Treatments for Chronic Hepatitis C Virus Infection, Am. J Gastroenterol., vol. 102, 2007, pp. 2332-2338.
Heck et al., Effects of Mutagenic and Chain-terminating Nucleotide Analogs on Enzymes Isolated from Hepatitis C Virus Strains of Various Genotypes, Antimicrob. Agents Chemother., vol. 52, 2008, pp. 1901-1911.
Howe et al., Molecular Mechanism of Hepatitis C Virus Replicon Variants with Reduced Susceptibility to a Benzofuran Inhibitor, HCV-796, Antimicrob. Agents Chemother., vol. 52, 2008, pp. 3327-3338.
Huang et al., X-ray Snapshot of the Mechanism-Based Inactivation of Human Neutrophil Elastase by 1, 2, 5-Thiadiazolidin-3-one 1, 1 Dioxide Derivatives, J Med Chem., vol. 51, 2008, pp. 2003-2008.
Ingallinella et al., Potent Peptide Inhibitors of Human Hepatitis C Virus NS3 Protease are Obtained by Optimizing the Cleavage Products, Biochemistry, 37, 1998, pp. 8906-8914.
International Search Report for PCT/US2009/058048, mailed Jun. 23, 2010 (13 pages).
International Preliminary Report on Patentability for PCT/US2009/058048, mailed Apr. 7, 2011 (8 pages).
Jin et al., Process Development of 1, 2-Benzisothiazolin-3(2H)-one by Replacing of the Toxic Materials, Synlett, vol. 13, 2003, pp. 1967-1968.
Kato et al., Production of Infectious Hepatitis C Virus of Various Genotypes in Cell Cultures, J Viral. , vol. 81, 2007, pp. 4405-4411.
Keller et al., A Practical View of Druggability, Curr. Opin. Chem. Biol., vol. 10, 2006, pp. 357-361.
Kerns et al., Pharmaceutical Profiling in Drug Discovery, Drug Discov. Today, vol. 8, 2003, pp. 316-323.
Kim et al., Crystal Structure of the Hepatitis C Virus NS3 Protease Domain Complexed with a Synthetic NS4A Cofactor Peptide, Cell, vol. 87, 1996, pp. 343-355.
Kim et al., Hepatitis C Virus NS3 RNA Helicase Domain with a Bound Oligonucleotide: the Crystal Structure Provides Insights into the Mode of Unwinding, Structure, vol. 6, 1998, pp. 89-100.
Koch et al., Recent Progress in the Development of Inhibitors of the Hepatitis C Virus RNA-Dependent RNA Polymerase, Curr. Topics Med. Chem., vol. 7, 2007, pp. 1302-1329.
Kolykhalov et al., Hepatitis C virus-encoded enzymatic activities and conserved RNA elements in the 3' non translated region are essential for virus replication in vivo, J Viral., vol. 74, 2000, pp. 2046-2205.
Korba et al., In vitro Evaluation of Combination Therapies Against Hepatitis B Virus Replication, Antiviral Res., vol. 29, 1995, pp. 49-51.
Korba et al., Nitazoxanide, Tizoxanide and Other Thiazolides Are Potent Inhibitors of Hepatitis B Virus and Hepatitis C Virus Replication, Antivir. Res., vol. 77, 2008, pp. 56-63.

(56) References Cited

OTHER PUBLICATIONS

Korba et al., Potential for Hepatitis C Virus Resistance to Nitazoxanide or Tizoxanide, Antimicrob. Agents Chemother., vol. 52, 2008, pp. 4069-4407.
Kuang et al., A General Inhibitor Scaffold for Serine Proteases with a (Chymo)trypsin-like Fold: Solution-Phase Construction and Evaluation of the First Series of Libraries of Mechanism-Based Inhibitors, J Am. Chem. Soc., vol. 121, 1999, pp. 8128-8129.
Kuang et al., Hepatitis C Virus NS3 RNA Helicase Activity is Modulated by the two Domains of NS3 and NS4A, Biochem. Biophys. Res. Commun., vol. 317, 2004, pp. 211-217.
Kwong et al., Structure and Function of Hepatitis C Virus NS3 Helicase, Curr. Top Microbiol. Immunol. , vol. 242, 2000, pp. 171-196.
Lam et al., Two Novel Conserved Motifs in the Hepatitis C Virus NS3 Protein Critical for Helicase Action, J Biol. Chem., vol. 278, 2003, pp. 44514-44524.
Lamanna et al., Straightforward Recursive Partitioning Model for Discarding Insoluble Compounds in the Drug Discovery Process, J Med Chem., vol. 51, 2008, pp. 2891-2897.
Lin et al., Discovery and Development ofVX-950, a Novel, Covalent and Reversible Inhibitor of Hepatitis C Virus NS3/NS4A Serine Protease, Infectious Disorders—Drug Targets, vol. 6, 2006, pp. 3-16.
Lin et al., The Role of Absorption, Distribution, Metabolism, Excretion and Toxicity in Drug Discovery, Curr. Top Med. Chem., vol. 3, 2003, pp. 1125-1154.
Lindenbach et al., Cell Culture-grown Hepatitis C Virus is Infectious in vivo and can be Recultured in vitro, Proc. Natl. Acad. Sci. U SA, vol. 103, 2006, pp. 3805-3809.
Lindenbach et al., Unravelling Hepatitis C Virus Replication from Genome to Function, Nature, vol. 436, 2005, pp. 933-938.
Lipinski, Drug-like Properties and the Causes of Poor Solubility and Poor Permeability, J Pharmacol. Toxicol. Methods, vol. 44, 2000, pp. 235-249.
Lohmann et al., Biochemical Properties of Hepatitis C Virus NS5B RNA-dependent RNA Polymerase and Identification of Amino Acid Sequence Motifs Essential for Enzymatic Activity, J Virol., vol. 71, 1997, pp. 8416-8428.
Lohmann et al., Processing Pathways of the Hepatitis C Virus Proteins, J Hepatol., vol. 24, 1996, pp. 11-19.
Ludmerer et al., Replication Fitness and NS5B Drug Sensitivity of Diverse Hepatitis C Virus Isolates Characterized by Using a Transient Replication Assay, Antimicrob. Agents Chemother. , vol. 49, 2005, pp. 2059-2069.
Lundquist et al., Improved Solid-Phase Peptide Synthesis Method Utilizing a-Azide Protected Amino Acids, Org. Lett., vol. 3, 2001, pp. 781-783.
Mathy et al., Combinations of Cyclophilin Inhibitor NIM811 with Hepatitis C Virus NS3-4A Protease or NS5B Polymerase Inhibitors Enhance Antiviral Activity and Suppress the Emergence of Resistance, Antimicrob. Agents Chemother., vol. 52, 2008, pp. 3267-3275.
Meanwell, Hepatitis C Virus Entry: An Intriguing Challenge for Drug Discovery, Curr. Opin. Investig. Drugs, vol. 7, 2006, pp. 727-732.
Moses et al., The Growing Applications of Click Chemistry, Chem. Soc. Rev., vol. 36, 2007, pp. 1249-1262.
Mueller et al., Characterization of the West Nile virus protease substrate specificity and inhibitors, The International Journal of Biochemistry and Cell Biology, vol. 39 issue 3, 2007, pp. 606-614.
Mueller et al., Identification and Biochemical Characterization of Small-Molecule Inhibitors of West Nile Virus Serine Protease by a High-Throughput Screen, Antimicrobial Agents and Chemotherapy, vol. 52 issue 9, 2008, pp. 3385-3393.
Njoroge et al., Challenges in Modern Drug Discovery: A Case Study of Boceprevir, an HCV Protease Inhibitor for the Treatment of Hepatitis C Infection, Ace Chem. Res., vol. 41, 2007, pp. 50-59.
O'Farrell et al., Substrate Complexes of Hepatitis C Virus RNA Polymerase (HC-J4): Structural Evidence for Nucleotide Import and De Novo Initiation, J Mol. Biol., vol. 326, 2003, pp. 1025-1035.
Okuse et al., Enhancement of Antiviral Activity Against Hepatitis C Virus In Vitro by Interferon Combination Therapy, Antivir. Res., vol. 65, 2005, pp. 23-34.
Paeshuyse et al., The Imidazopyrrolopyridine Analogue AG110 is a Novel, Highly Selective Inhibitor of Pestiviruses The Imidazopyrrolopyridine Analogue AG110 is a Novel, Highly Selective Inhibitor of Pestiviruses, Journal of Virology vol. 81(20), 2007, pp. 11046-11053.
Patchett, Priveleged Structures—an Update, Ann. Rep. Med. Chem., vol. 35, 2000, pp. 289-304.
Perni et al., Preclinical Profile of VX-950, a Potent, Selective, and Orally Bioavailable Inhibitor of Hepatitis C Virus NS3-4A Serine Protease, Antimicrob. Agents Chemother. , vol. 50, 2006, pp. 899-909.
Perz et al., The Contributions of Hepatitis B Virus and Hepatitis C Virus Infections to Cirrhosis and Primary Liver Cancer Worldwide, J Hepatol., vol. 45, 2006, pp. 529-538.
Pierra et al., Nm 283, an Efficient Prodrug of the Potent anti-HCV Agent 2'-C-Methylcytidine, Nucleosides Nucleotides Nucleic Acids, vol. 24, 2005, pp. 767-770.
Poumbourios et al., Recent Advances in our Understanding of Receptor Binding, Viral Fusion, and Cell Entry of Hepatitis C Virus: New Targets for the Design of Antiviral Agents, Antiviral Chem. Chemother., vol. 18, 2007, pp. 169-189.
Proudfoot, Drugs, Leads and Drug-likeness. An Analysis of Some Recently-Launched Drugs, Bioorg. Med. Chem. Lett., vol. 12, 2002, pp. 1647-1650.
Puig-Basagoiti et al., Triaryl Pyrazoline Compound Inhibits Flavivirus RNA Replication, Antimicrobial Agents and Chemotherapy, vol. 50(4), 2006, pp. 1320-1329.
Ranganathan et al., The Design and Synthesis of Redox Core-alpha Amino Acid Composites Based on Thiol Disulfide Exchange Mechanism and a Comparative Study of their Zinc Abstraction Potential from [CCXX] Boxes in Proteins, Tetrahedron, vol. 58, 2002, pp. 2861-2874.
Rishton, Nonleadlikeness and Lead Likeness in Biochemical Screening, Drug Discov. Today, vol. 8, 2003, pp. 86-96.
Ronn et al., New Developments in the Discovery of Agents to Treat Hepatitis C, Curr. Topics Med. Chem., vol. 8, 2008, pp. 533-562.
Roper et al., Click Chemistry for Drug Discovery, Methods-Principles Med Chem., vol. 34, 2006, pp. 313-339.
Rosales-Leon et al., Analysis of the domain interactions between the protease and helicase of NS3 in dengue and hepatitis C virus, J Mol. Graph Model, vol. 25, 2007, pp. 585-594.
Rostovtsev et al., A Stepwise Huisgen Cycloaddilion Process: Copper (I)-Catalyzed Regioselective Ligation of Azides and Terminal Alkynes, Angew Chem. Int. Ed., vol. 41, 2002, pp. 2596-2599.
Schechter et al., On the Size of the Active Site in Proteases: Papain, Biochem. Biophys. Res. Comm., vol. 27, 1967, pp. 157-162.
Schmidt-Mende et al., Determinants for Membrane Association of the Hepatitis C Virus RNA-Dependent RNA Polymerase, J Biol. Chem., vol. 276, 2001, pp. 44052-44063.
Schmitz et al., NS5A—From Obscurity to New Target for HCV Therapy, Recent Adv. Anti-Infective Drug Discov. , vol. 3, 2008, pp. 77-92.
Sebastian et al., N-methylisatin-beta-thiosemicarbazone derivative (SCH 16) is an inhibitor of Japanese encephalitis virus infection in vitro and in vivo, Virology Journal, vol. 5 issue 64, 2008, pp. 1-12.
Serebrov et al., Establishing a Mechanistic Basis for the Large Kinetic Steps of the NS3 Helicase, J Biol. Chem., vol. 284, 2008, pp. 2512-2521.
Sheldon et al., Novel Protease and Polymerase Inhibitors for the Treatment of Hepatitis C Virus Infection, Expert Opin. Investig. Drugs, vol. 18, 2007, pp. 1171-1181.
Shen et al., Histone Deacetylase Inhibitors Through Click Chemistry, J Med. Chem., vol. 51, 2008, pp. 7417-7427.
Shim et al., Recent Patents on Nucleoside and Nucleotide Inhibitors for HCV Recent Patents, Anti-infect Drug Disc vol. 1, 2006, pp. 323-331.
Singh, Preclinical Pharmacokinetics: An Approach Towards Safer and Efficacious Drugs, Curr. Drug Metab. vol. 7, 2006, pp. 165-182.
Soriano et al., Emerging Drugs for Hepatitis C, Expert Opin. Emerging Drugs, vol. 13, 2008, pp. 1-19.

(56) References Cited

OTHER PUBLICATIONS

Tong et al., Identification and Analysis of Fitness of Resistance Mutations Against the HCV Protease Inhibitor SCH 503034, Antiviral Res., vol. 70, 2006, pp. 28-38.
Tornoe et al., Peptidotriazoles on Solid Phase: [1 ,2,3]-Triazoles by Regiospecific Copper (I)-Catalyzed 1 ,3-Dipolar Cycloadditions of Terminal Alkynes to Azides, J Org Chem., vol. 67, 2002, pp. 3057-3064.
Trainor, Plasma Protein Binding and the Free Drug Principle: Recent Developments and Applications, Ann. Rep. Med. Chem., vol. 42, 2007, pp. 489-502.
Veber, Molecular Properties that Influence the Oral Bioavailability of Drug Candidates, J Med Chem., vol. 45, 2002, pp. 2615-2623.
Wakita et al., Production of infectious hepatitis C virus in tissue culture from a cloned viral genome, Nature Medicine, 2005, vol. 11, No. 7: 791-796.
Waterbeemd et al., Property-Based Design: Optimization of Drug Absorption and Pharmacokinetics, J Med. Chem., vol. 44, 2001, pp. 1313-1333.
Wei et al., Mechanism-Based Inactivation of Human Leukocyte Elastase via an Enzyme-Induced Sulfonamide Fragmentation Process, Arch Biochem. Biophys. , vol. 429, 2004, pp. 60-70.
Williams et al., Toxicophores: Groups and metabolic Routes Associated with Increased Safety Risk, Curr. Opin. Drug Discov. Develop, vol. 5, 2002, pp. 104-115.
Williams, Toxicophores: Investigations in Drug Safety, Toxicology, vol. 226, 2006, pp. 1-11.
Winum, Therapeutic Potential of Sulfamides as Enzyme Inhibitors, Med. Res. Revs., vol. 26, 2006, pp. 767-792.
Wunberg, Improving the Hit-to-Lead process: Data-driven Assessment of Drug-like and Lead-like Screening Hits, Drug Discov. Today, vol. 11, 2006, pp. 175-180.
Yang et al., Inhibition of Serine Proteases by a New Class of Cyclosulfamide-Based Carbamylating Agents, Arch. Biochem. Biophys., vol. 475, 2008, pp. 115-120.
You et al., A Novel in Vitro Replication System for Dengue Virus, J Biol. Chem., vol. 274, 1999, pp. 33714-33722.
Zapf et al., Recent Progress on Novel HCV Inhibitors, Ann. Rep. Med. Chem., vol. 42, 2007, pp. 281-300.
Zhang et al., Ruthenium-Catalyzed Cycloaddition of Alkynes and Organic Azides, J Am. Chem. Soc., vol. 127, 2005, pp. 15998-15999.
Zhao, Scaffold Selection and Scaffold Hopping in Lead Generation: a Medicinal Chemistry Perspective, Drug Discov Today, vol. 12, 2007, pp. 149-155.
Zhong et al., Potential Protease Inhibitors Based on a Functionalized Cyclic Sulfamide Scaffold, J Comb. Chem., vol. 6, 2004, pp. 556-563.
Zhong et al., Recent Developments in the Design of Mechanism-Based and Alternate Substrate Inhibitors of Serine Proteases, Curr. Top Med. Chem., vol. 4, 2004, pp. 1203-1216.
Zhong et al., Serendipitous Discovery of an Unusual Rearrangement Leads to Two New Classes of Potential Protease Inhibitors, Bioorg. Med. Chem., vol. 12, 2004, pp. 6249-6254.

FLAVIVIRUS INHIBITORS AND METHODS OF THEIR USE

CROSS REFERENCE TO RELATED APPLICATIONS

The present application is a continuation of U.S. Ser. No. 13/120,583, filed Jun. 1, 2011, which claims the benefit of U.S. Provisional Application No. 61/099,411, filed Sep. 23, 2008, both applications of which are hereby incorporated by reference in their entireties.

STATEMENT REGARDING FEDERALLY FUNDED RESEARCH

This invention was made with government support under Grant Nos. R21-AI-57705, R01-AI 070791, and U54 AI57168 awarded by the National Institutes of Health (National Institute of Allergy and Infectious Diseases). The government has certain rights in the invention.

BACKGROUND

*Flaviviruses* such as West Nile virus (WNV), Japanese Encephalitis virus, and Dengue virus (e.g., the four known serotypes of Dengue virus (DEN-1-4)) are significant human pathogens that cause millions of infections each year and result in considerable morbidity and mortality. DEN viruses cause a simple and self-limiting disease in humans called dengue fever (DF), which often resolves in a week to 10 days. However, more severe forms of the disease, known as Dengue hemorrhagic fever (DHF) and Dengue shock syndrome (DSS) common in areas endemic to DEN 1-4 lead to considerable morbidity and mortality. According to World Health Organization estimates, 50-100 million cases of DEN infections in tropical and subtropical countries occur each year. WNV was introduced into the western hemisphere during an outbreak in the United States in 1999. In the following years, WNV has spread throughout much of North America and has become a public health concern. Most WNV infections are asymptomatic; however, about 20% of cases are associated with mild flu-like symptoms. A small fraction of these cases progress to more severe clinical manifestations including encephalitis and/or flaccid paralysis. Currently, there are no approved vaccines or antiviral therapeutics available for either DEN- or WNV-infected humans.

SUMMARY

Novel methods and compositions for treating *Flavivirus* infections are provided. The methods comprise administering to a subject a therapeutically effective amount of a *Flavivirus* inhibitor are disclosed. For example, a method of treating a *Flavivirus* infection in a subject is disclosed that includes administering to the subject a therapeutically effective amount of a compound of the following formula:

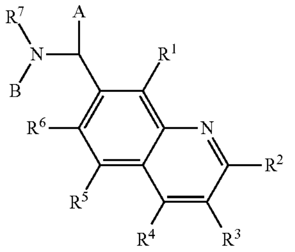

or pharmaceutically acceptable salts and prodrugs thereof. In this compound, $R^1$, $R^2$, $R^3$, $R^4$, $R^5$, and $R^6$ are each independently selected from hydrogen, hydroxyl, substituted or unsubstitited $C_{1-4}$ alkyl, substituted or unsubstitited $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen; A is selected from substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; B is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^7$ is hydrogen or an attachment for a cyclic B group. This compound is disclosed with the proviso that $R^1$ is not OH if
A is

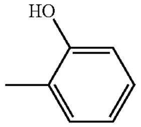 and B is 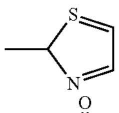, or

A is 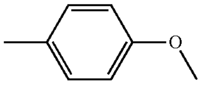 and B is 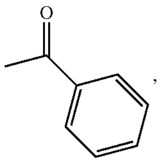, or

A is 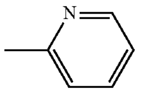 and B is 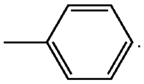.

Also provided is a method of treating a *Flavivirus* infection in a subject that includes administering to the subject a therapeutically effective amount of a compound of the following formula:

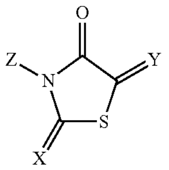

or pharmaceutically acceptable salts and prodrugs thereof. In this compound, X is S or $NR^1$, wherein $R^1$ is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; Y is $R^1$ or $(CH)R^1$; and Z is $R^1$, or

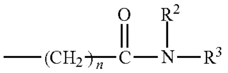

wherein n is 0 to 4, $R^2$ is $R^1$, and $R^3$ is $R^1$, or

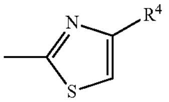

wherein $R^4$ is hydroxyl or $R^1$.

Also provided is a method of treating a *Flavivirus* infection in a subject that includes administering to the subject a therapeutically effective amount of a compound of the following formula:

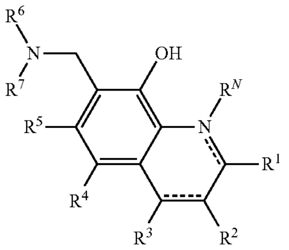

or a pharmaceutically acceptable salt or prodrug thereof. In this compound,  is a single or double bond, and $R^N$ is hydrogen or substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ heteroalkenyl, substituted or unsubstituted $C_{2-6}$ alkynyl, substituted or unsubstituted $C_{2-6}$ heteroalkynyl when is a single bond and $R^N$ is absent when is a double bond; $R^3$, $R^4$, and $R^5$ are each independently selected from hydrogen, hydroxyl, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen; and $R^6$ and $R^7$ are each independently selected from substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, wherein $R^6$ and $R^7$ may combine to form a substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Also provided is a compound for use in treating a *Flavivirus* infection with the following formula:

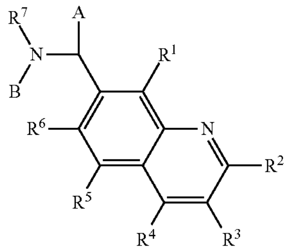

or pharmaceutically acceptable salts and prodrugs thereof. In this compound, $R^1$, $R^2$, $R^3$, $R^4$, $R^5$, and $R^6$ are each independently selected from hydrogen, hydroxyl, substituted or unsubstitited $C_{1-4}$ alkyl, substituted or unsubstitited $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen; A is selected from substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; B is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and $R^7$ is hydrogen or an attachment for a cyclic B group. This compound is disclosed with the proviso that $R^1$ is not OH if A is

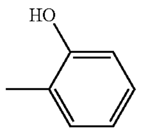

and B is

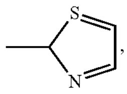, or

A is

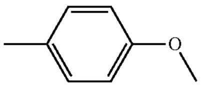

and B is

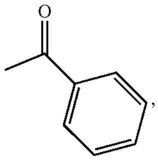, or

A is

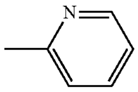 and B is 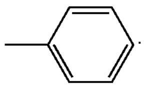.

Further provided is a compound for use in treating a *Flavivirus* infection with the following formula:

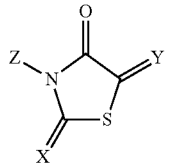

or pharmaceutically acceptable salts and prodrugs thereof. In this compound, X is S or $NR^1$, wherein $R^1$ is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; Y is $R^1$ or $(CH)R^1$; and Z is $R^1$, or

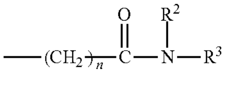

wherein n is 0 to 4, $R^2$ is $R^1$, and $R^3$ is $R^1$, or

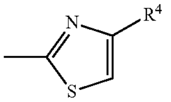

wherein $R^4$ is hydroxyl or $R^1$.

Additionally provided is a compound for use in treating a *Flavivirus* infection with the following formula:

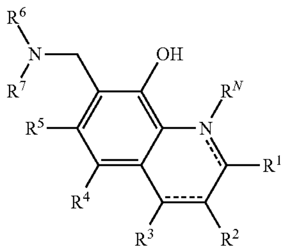

or a pharmaceutically acceptable salt or prodrug thereof. In this compound, - - - - - is a single or double bond, and $R^N$ is hydrogen or substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ heteroalkenyl, substituted or unsubstituted $C_{2-6}$ alkynyl, substituted or unsubstituted $C_{2-6}$ heteroalkynyl when is a single bond and $R^N$ is absent when

is a double bond; $R^3$, $R^4$, and $R^5$ are each independently selected from hydrogen, hydroxyl, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen; and $R^6$ and $R^7$ are each independently selected from substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, wherein $R^6$ and $R^7$ may combine to form a substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Other compounds are provided for use in the methods described herein.

DETAILED DESCRIPTION

Figure 1:
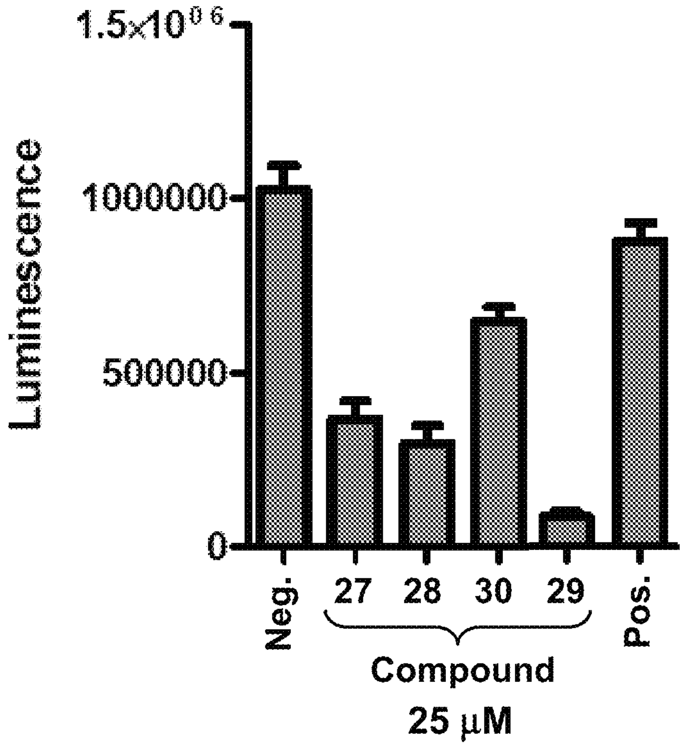
FIG. 1 is a bar graph showing WNV replicon inhibition assay results.

Methods of treating a *Flavivirus* infection in a subject comprising administering to the subject a therapeutically effective amount of novel *Flavivirus* inhibitors, e.g., *Flavivirus* serine protease inhibitors, are disclosed. These methods are useful in treating, preventing, and/or ameliorating *Flavivirus* infections such as, for example, West Nile Virus, Dengue Virus, and Japanese Encephalitis Virus.

A first group of *Flavivirus* inhibitors useful in the methods described herein comprises compounds represented by Compound I:

I

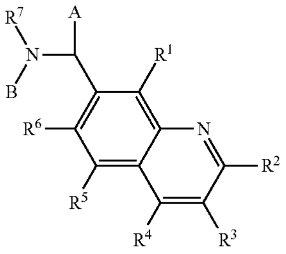

or a pharmaceutically acceptable salt or prodrug thereof.

In Compound I, $R^1$, $R^2$, $R^3$, $R^4$, $R^5$, and $R^6$ are each independently selected from hydrogen, hydroxyl, substituted or unsubstitited $C_{1-4}$ alkyl, substituted or unsubstitited $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen.

Also, in Compound I, A is selected from substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Additionally, in Compound I, B is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Further, in Compound I, $R^7$ is hydrogen or an attachment for a cyclic B group. When $R^7$ is an attachment for a cyclic B group, a ring structure is formed that includes $R^7$, B and the nitrogen to which $R^7$ and B are attached, i.e., a heterocyclic molecule is formed. An example of such a configuration of Compound I has the following Structure I-A:

I-A

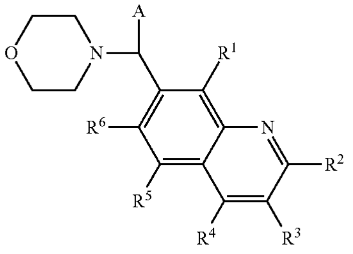

However, Compound I has the proviso that $R^1$ is not OH if A is or

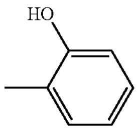

and B is

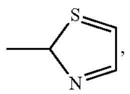

,

A is or

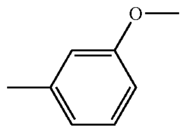

and B is

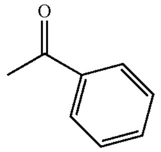

,

A is

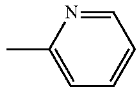

and B is

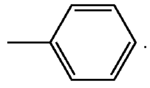

.

Examples of the A group include:

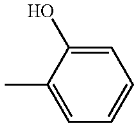

,

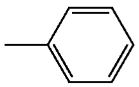

, and

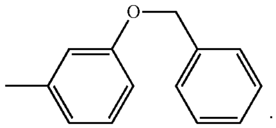

.

The -B group of Compound I can have, for example, the following Structure A1:

A1

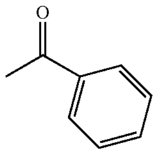

Additionally, the -B group of Compound I can have, for example, the following Structure A2:

A2

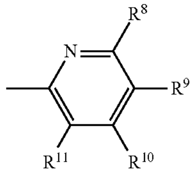

wherein $R^8$, $R^9$, $R^{10}$, and $R^{11}$ are each independently $R^1$. Examples of Structure A2 include:

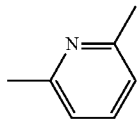

and

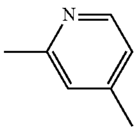

.

Further, the -B group of Compound I can have, for example, the following Structure A3:

A3

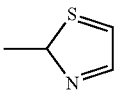

.

In addition, the -B group of Compound I can have, for example, the following Structure A4:

A4

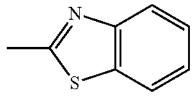

Examples of *Flavivirus* inhibitors represented by Compound I are as follows:

-continued
1
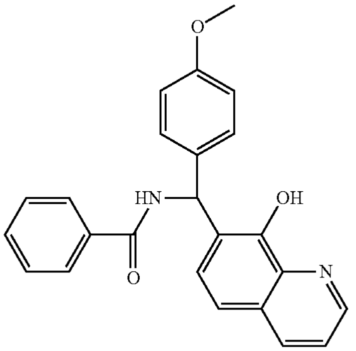
2
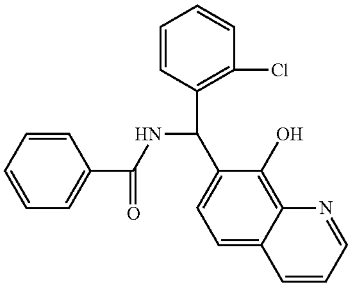
3
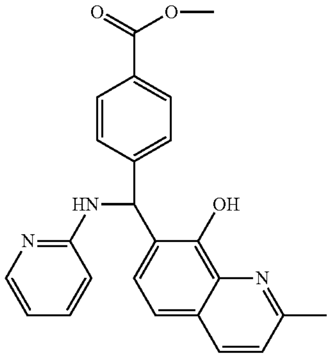
4
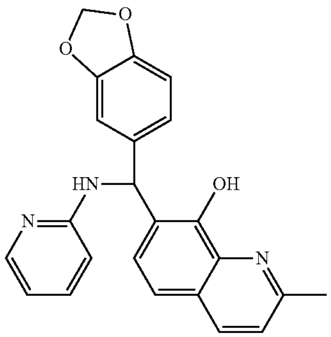
5
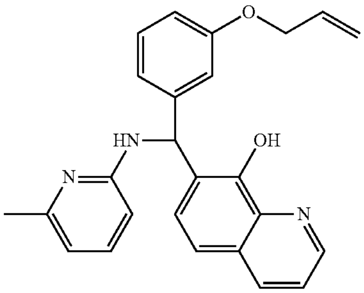
6
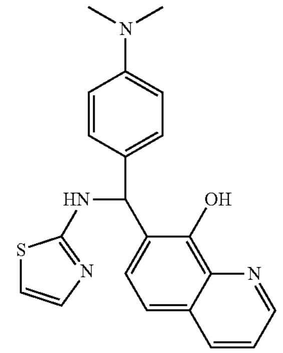
7
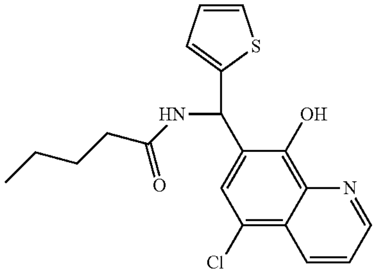
8
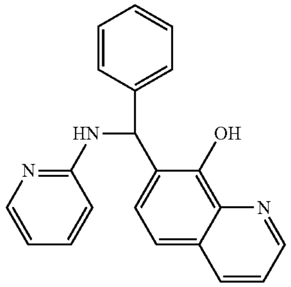
9
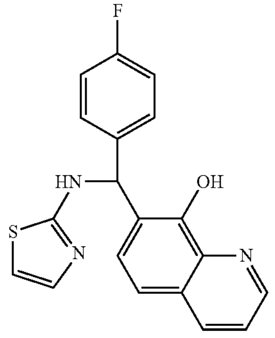
10
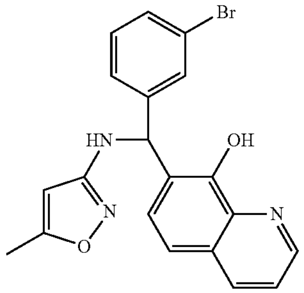

-continued

11

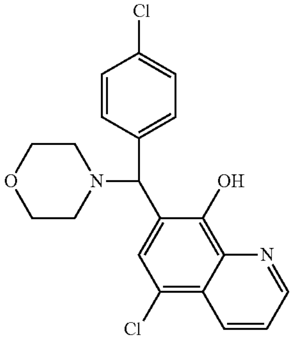

12

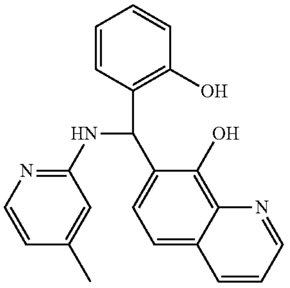

13

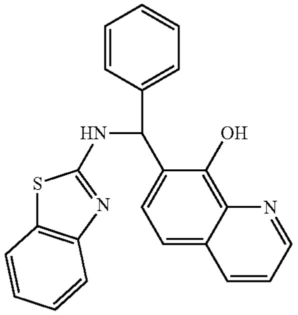

14

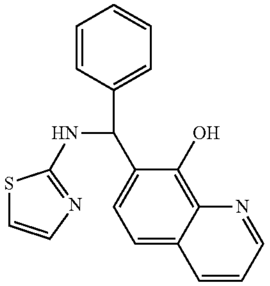

15

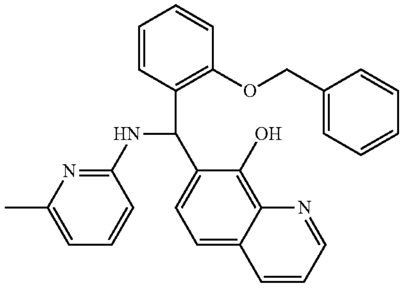

-continued

16

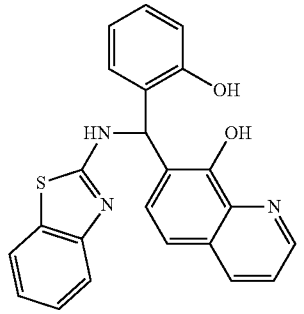

17

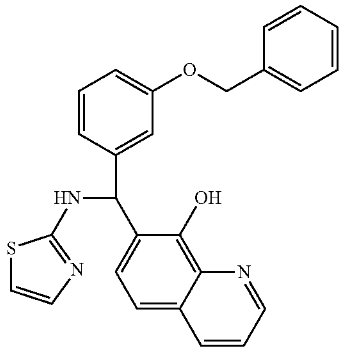

A second group of *Flavivirus* inhibitors useful in the methods described herein comprises compounds represented by Compound II:

II

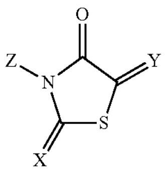

or a pharmaceutically acceptable salt or prodrug thereof.

In Compound II, X is S or $NR^1$, wherein $R^1$ is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, substituted or unsubstituted $C_{2-12}$ heteroalkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Also, in Compound II, Y is $R^1$ or $(CH)R^1$.

Additionally, in Compound II, Z is $R^1$, or

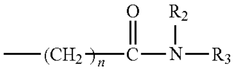

wherein n is 0 to 4, $R^2$ is $R^1$, and $R^3$ is $R^1$, or

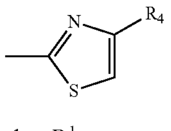

wherein $R^4$ is hydroxyl or $R^1$.

The —Y group of Compound II can have, for example, the following Structure B1:

B1

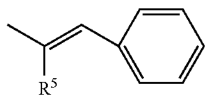

wherein $R^5$ is $R^1$.

Additionally, the —Y group of Compound II can have, for example, the following Structure B2:

B2

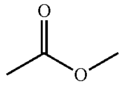

Further, the —Y group of Compound II can have, for example, the following Structure B3:

B3

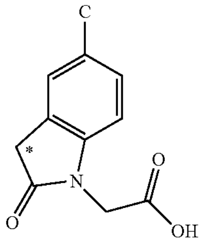

wherein * indicates the carbon through which this —Y group is connected to Compound II and C is a halogen (see, for example, compound 25 below).

Also, the —Y group of Compound II can have, for example, the following Structure B4:

B4

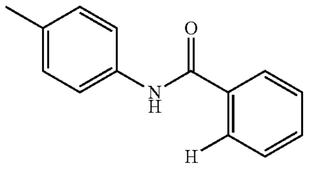

wherein H is a halogen.

Additionally, the —Y group of Compound II can have, for example, the following Structure B5:

B5

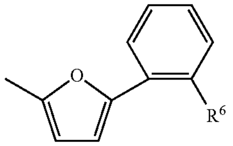

wherein $R^6$ is $R^1$.

Examples of *Flavivirus* inhibitors represented by Compound II are as follows:

18

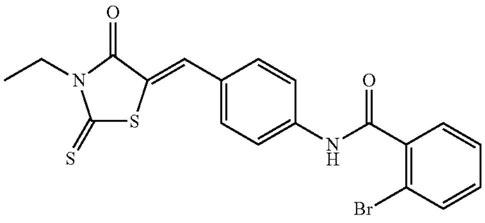

19

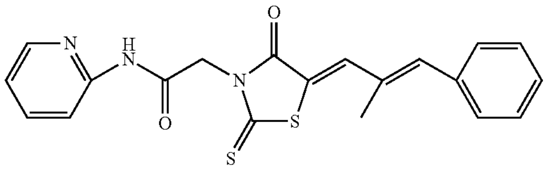

20

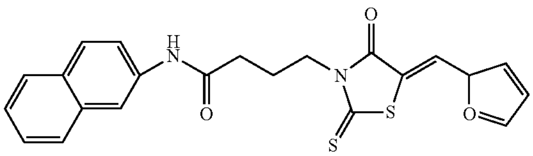

21

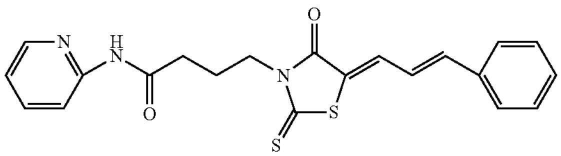

22

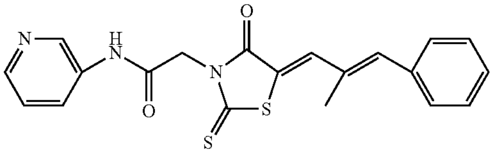

23

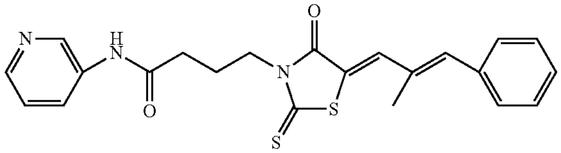

24

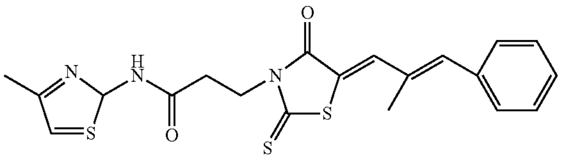

25

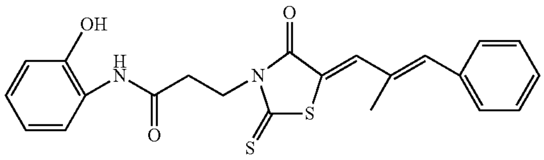

-continued

26

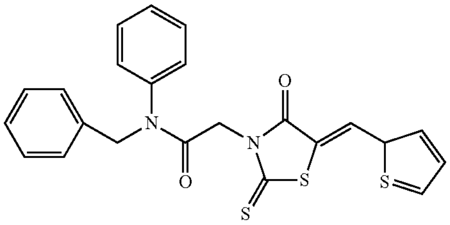

27

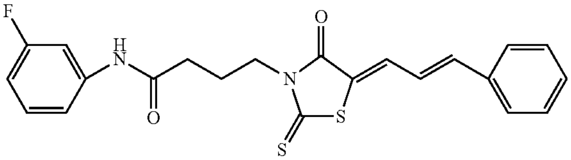

28

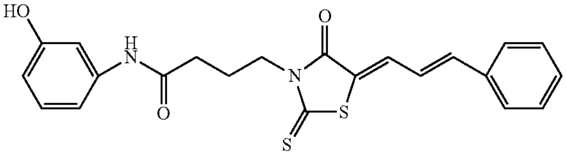

29

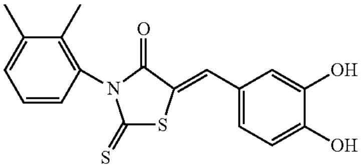

30

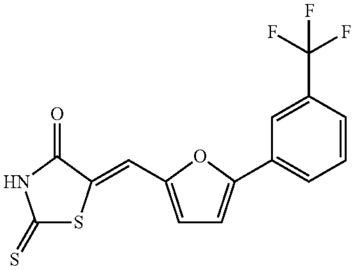

31

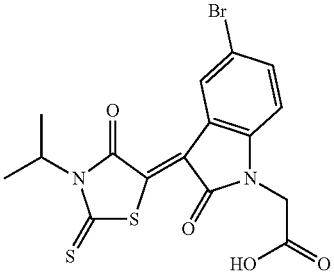

32

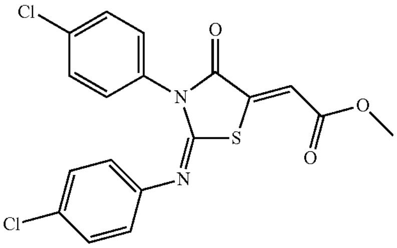

A third group of *Flavivirus* inhibitors useful in the methods described herein comprises compounds represented by Compound III:

III

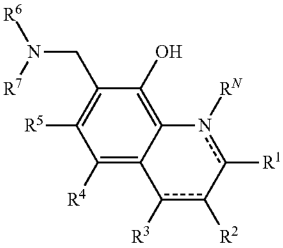

or a pharmaceutically acceptable salt or prodrug thereof.

In this Compound III,  is a single or double bond, and $R^N$ is hydrogen or substituted or unsubstituted $C_{1-6}$ alkyl, substituted or unsubstituted $C_{1-6}$ heteroalkyl, substituted or unsubstituted $C_{2-6}$ alkenyl, substituted or unsubstituted $C_{2-6}$ heteroalkenyl, substituted or unsubstituted $C_{2-6}$ alkynyl, substituted or unsubstituted $C_{2-6}$ heteroalkynyl when is a single bond and $R^N$ is absent when is a double bond.

Also in Compound III, $R^1$, $R^2$, $R^3$, $R^4$, and $R^5$ are each independently selected from hydrogen, hydroxyl, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen.

Additionally in Compound III, $R^6$ and $R^7$ are each independently selected from substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, wherein $R^6$ and $R^7$ may combine to form a substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

The $R^6$ and $R^7$ groups of Compound III can be, for example, ethyl groups.

Further, the $R^6$ and $R^7$ groups of Compound III can combine to form the following Structure C1:

C1

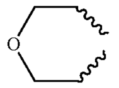

Also in Compound III, $R^4$ can be chloride.

Examples of *Flavivirus* inhibitors represented by Compound III are as follows:

33

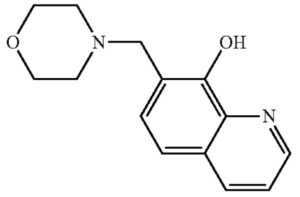

34

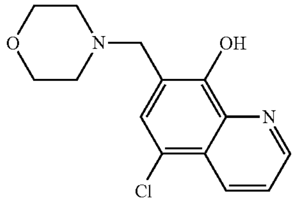

35

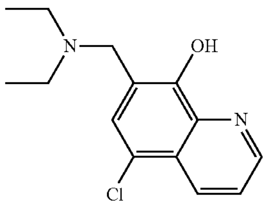

36

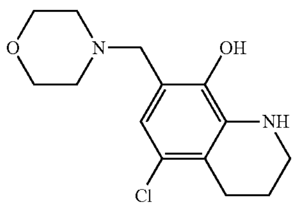

Additional *Flavivirus* inhibitors useful in the methods described herein have also been identified that may not be represented by Compound I, Compound II, or Compound III. The structures of these *Flavivirus* inhibitors are as follows:

37

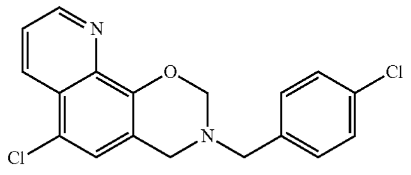

38

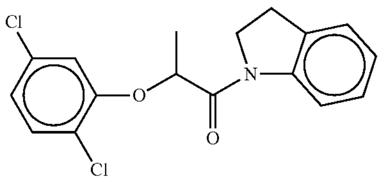

39

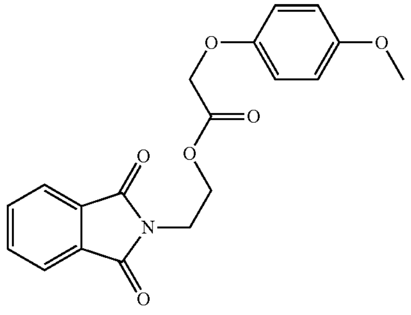

40

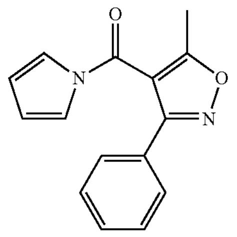

41

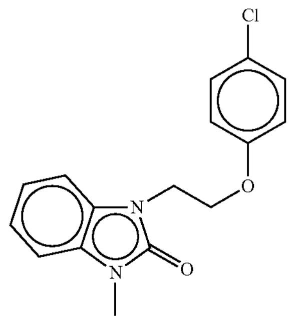

42

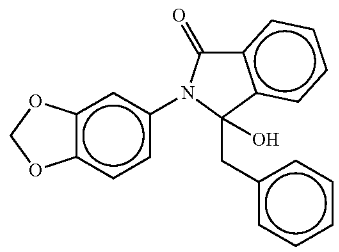

-continued
43
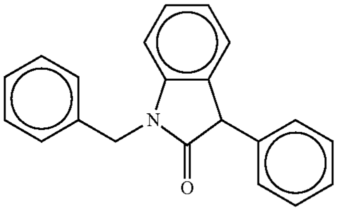
44
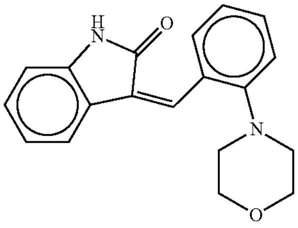
45
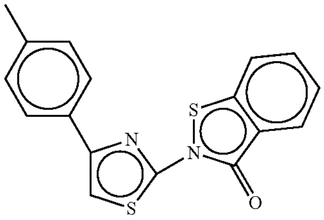
46
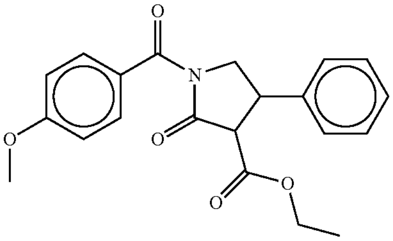
47
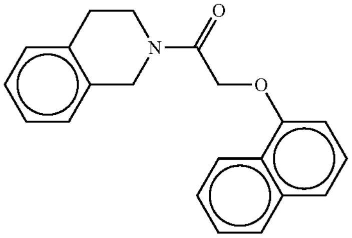
48
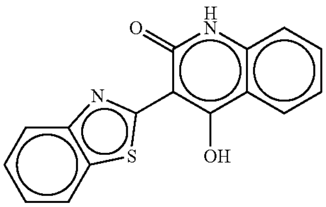
-continued
49
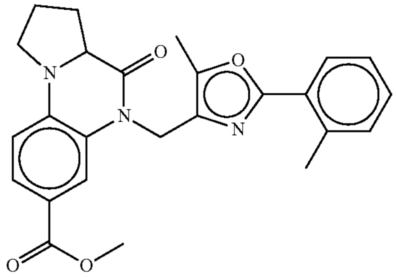
50
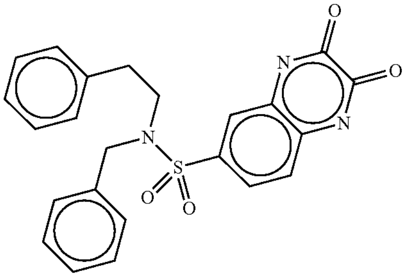
51
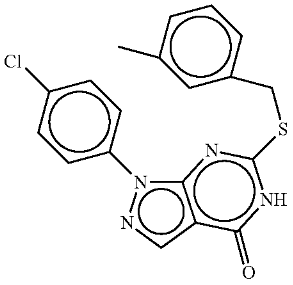
52
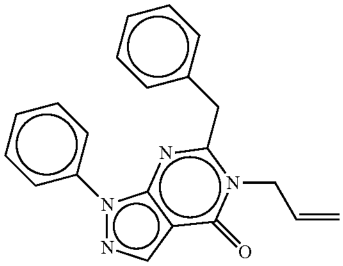
53
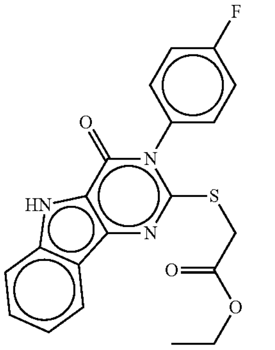

-continued
54
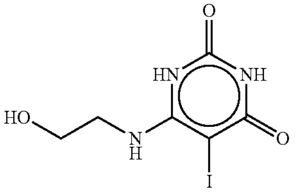
55
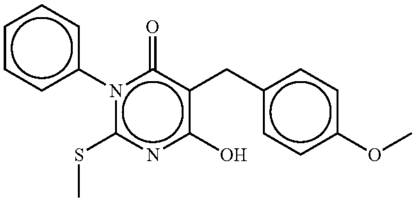
56
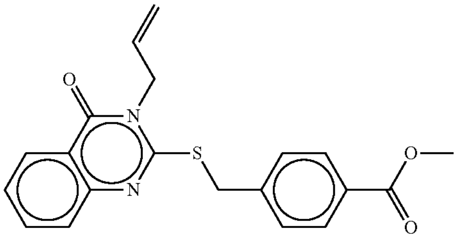
57
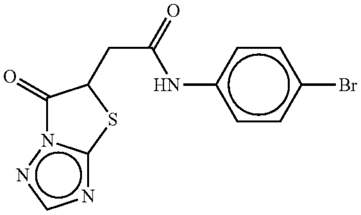
58
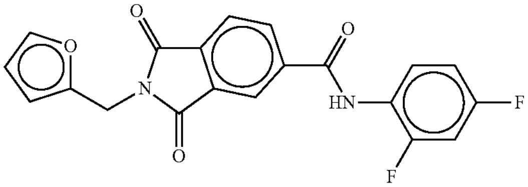
59
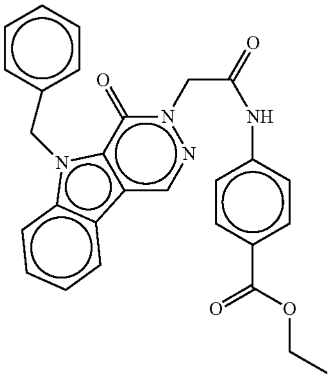
-continued
60
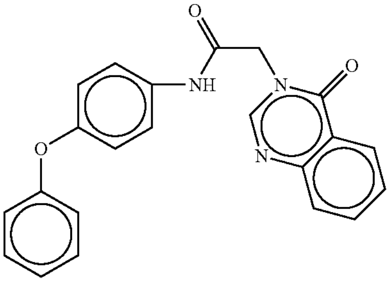
61
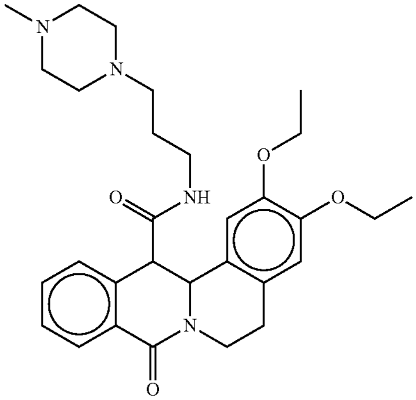
62
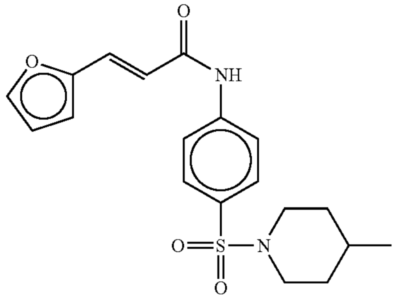
63
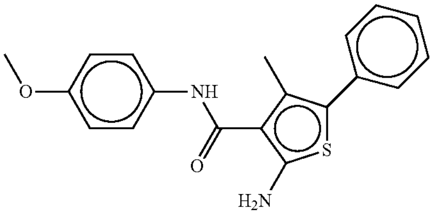
64
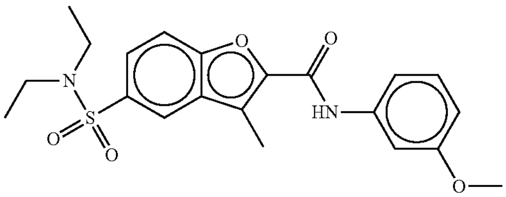

-continued
65
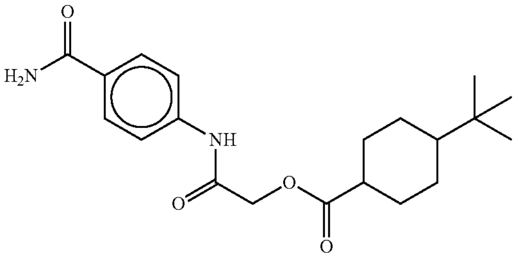
66
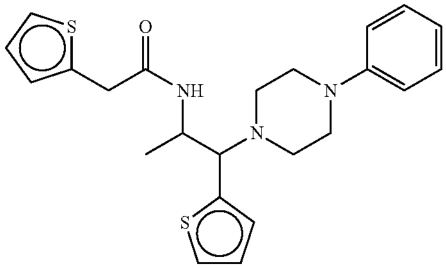
67
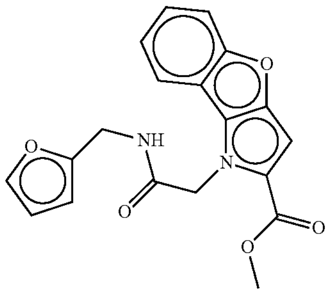
68
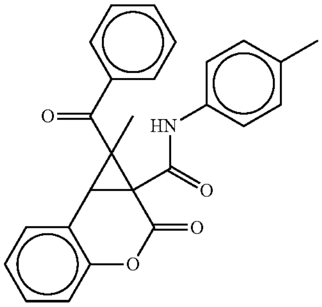
69
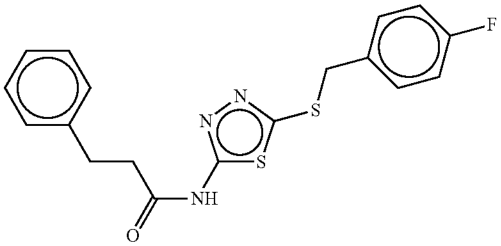
-continued
70
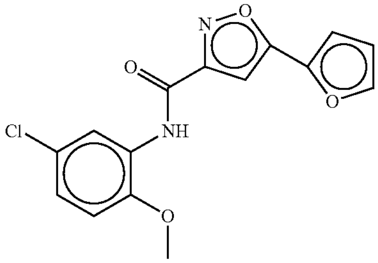
71
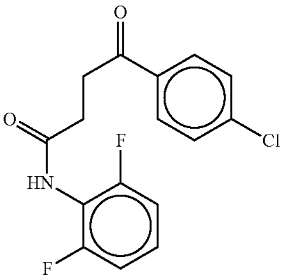
72
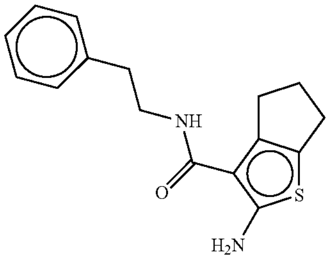
73
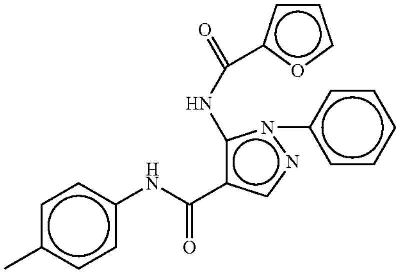
74
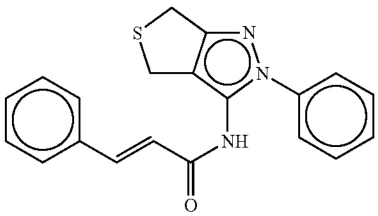
75
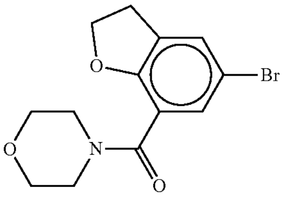

-continued
76
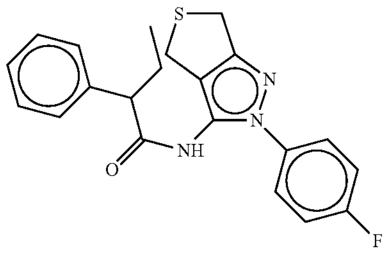
77
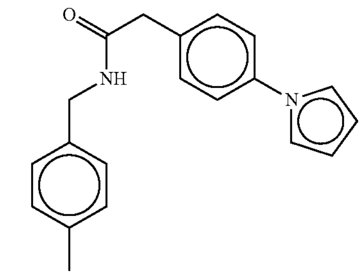
78
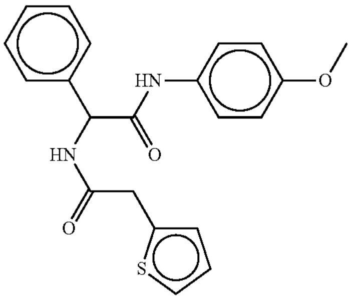
79
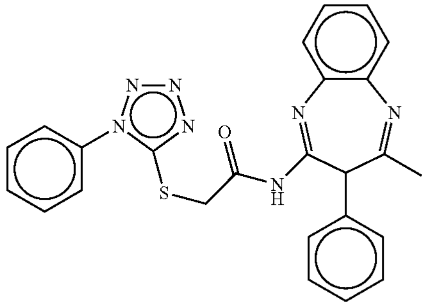
80
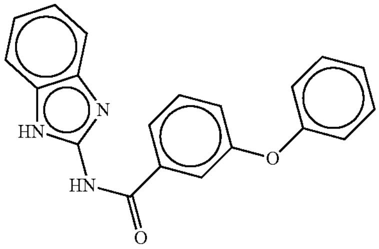
-continued
81
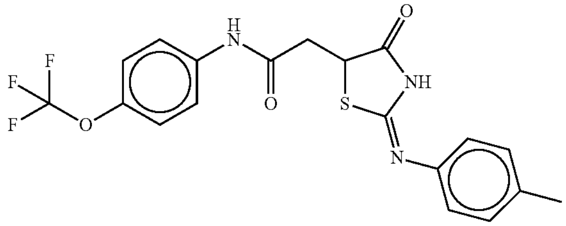
82
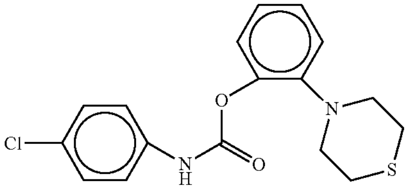
83
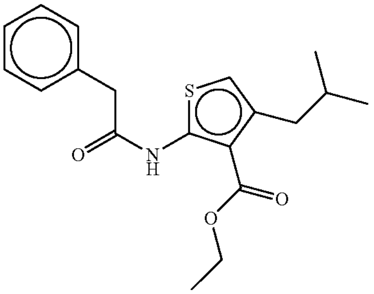
84
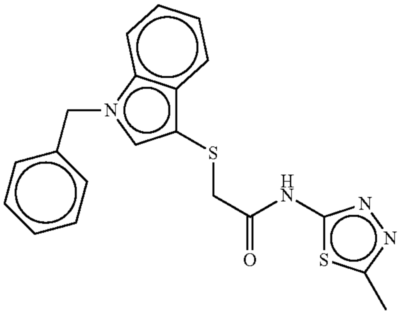
85
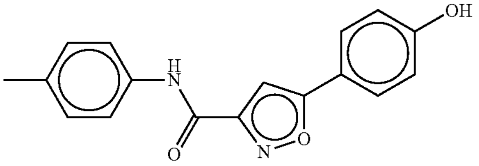
86
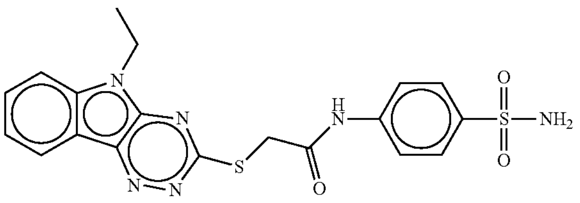

-continued
87
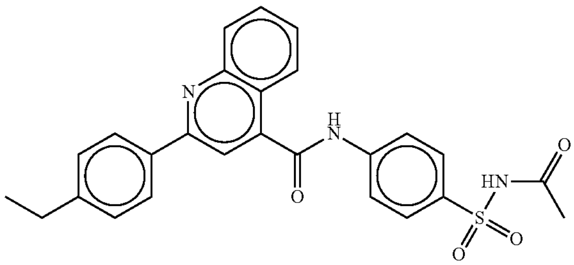
88
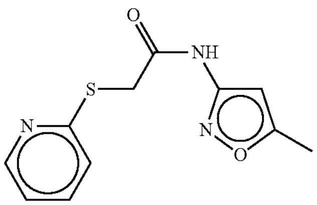
89
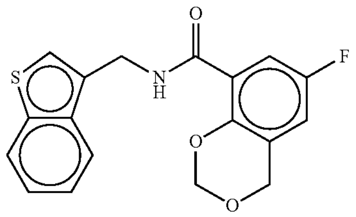
90
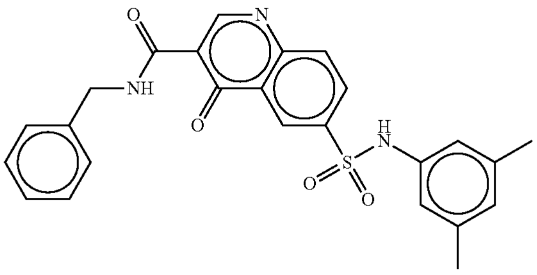
91
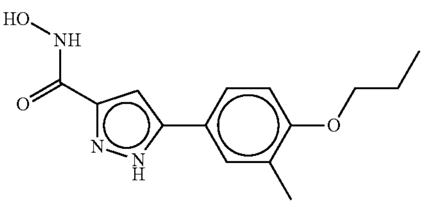
92
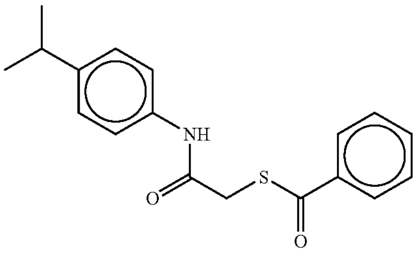
-continued
93
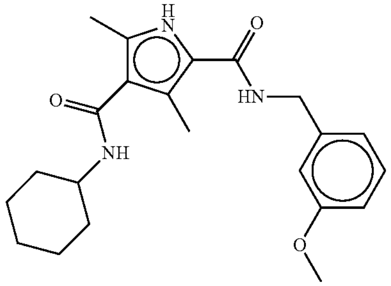
94
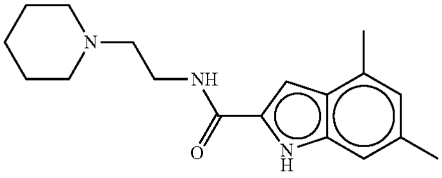
95
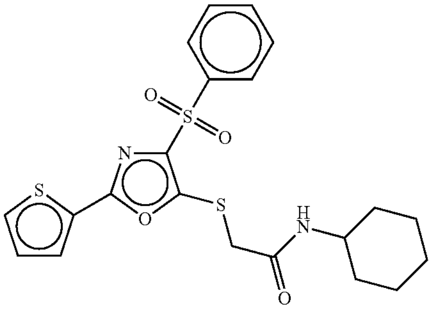
96
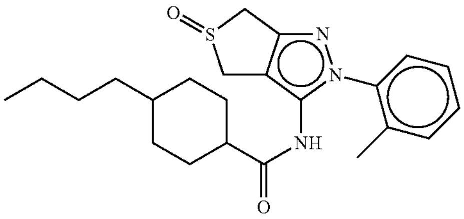
97
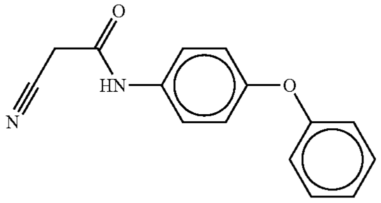
98
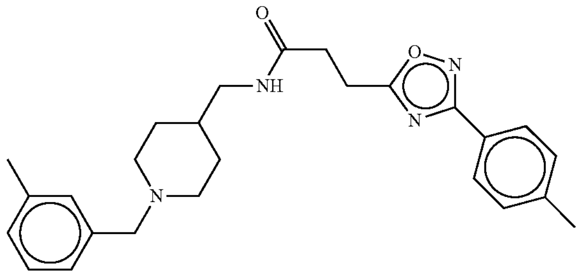

-continued

99

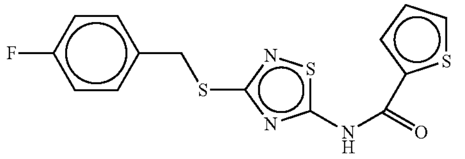

100

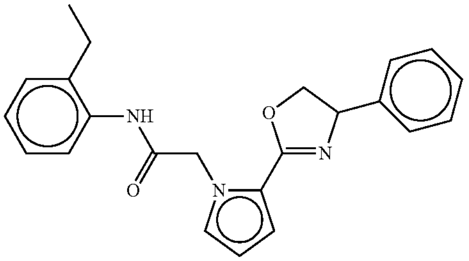

101

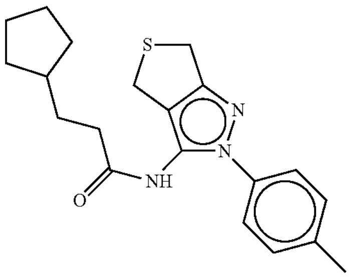

The compounds described herein can be prepared in a variety of ways known to one skilled in the art of organic synthesis. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on Compound I, Compound II, Compound III, and the additional *Flavivirus* inhibitors described above include the addition, subtraction, or movement of the various constituents as described for each compound. Similarly, when one or more chiral centers is present in a molecule the chirality of the molecule can be changed. Additionally, compound synthesis can involve the protection and deprotection of various chemical groups. The use of protection and deprotection, and the selection of appropriate protecting groups can be readily determined by one skilled in the art. The chemistry of protecting groups can be found, for example, in Wuts and Greene, Protective Groups in Organic Synthesis, $4^{th}$ Ed., Wiley & Sons, 2006, which is incorporated herein by reference in its entirety. The synthesis and subsequent testing of various compounds as described by Compound I, Compound II, Compound III, and the additional *Flavivirus* inhibitors described above to determine efficacy is contemplated.

As used herein, the terms alkyl, alkenyl, alkynyl, and cycloalkyl include straight- and branched-chain and cyclic monovalent substituents. Examples include methyl, ethyl, isobutyl, cyclohexyl, cyclopentylethyl, 2-propenyl, 3-butynyl, and the like. Heteroalkyl, heteroalkenyl, heteroalkynyl, and heterocycloalkyl are similarly defined but may contain O, S or N heteroatoms or combinations thereof within the backbone residue. The terms cycloalkylalkyl and heterocycloalkylalkyl are similarly defined The term aryl refers to a monocyclic or fused bicyclic moiety such as phenyl or naphthyl and the term heteroaryl refers to monocyclic or fused bicyclic ring systems containing one or more heteroatoms selected from O, S and N. Heteroaryls include 5-membered rings as well as 6-membered rings. Thus, aryl and heteroaryl systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Similarly, the terms arylalkyl and heteroarylalkyl refer to aryl and heteroaryl systems which are coupled to another residue through a carbon chain, including substituted or unsubstituted, saturated or unsaturated, carbon chains. The term substituted indicates the main substituent has attached to it one or more additional components, such as, for example, OH, halogen, or one of the substituents listed above.

Reactions to produce the compounds described herein can be carried out in solvents which can be readily selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatograpy (HPLC) or thin layer chromatography.

The compounds described herein or pharmaceutically acceptable salts or prodrugs thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein or a pharmaceutically acceptable salt or prodrug thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compounds described herein or pharmaceutically acceptable salts or prodrugs thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein or a pharmaceutically acceptable salt or prodrug thereof include capsules, tablets, pills, powders, and granules. In such solid dosage forms, the compounds described herein or a pharmaceutically acceptable salt or prodrug thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically acceptable salts or prodrugs thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compounds described herein that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Berge et al., *J. Pharm. Sci.* (1977) 66:1-19 which is incorporated herein by reference in its entirety, at least, for compositions taught herein.)

The methods described above are useful for treating *Flavivirus* infections in humans, e.g., including pediatric and geriatric populations, and animals, e.g., veterinary applications. The methods described herein comprise administering to a subject a therapeutically effective amount of the compounds described herein or a pharmaceutically acceptable salt or prodrug thereof. *Flavivirus* infections include, for example, West Nile Virus, Dengue Virus, and Japanese Encephalitis Virus. Several serotypes of Dengue Virus have been identified such as, for example, serotype DEN-1, serotype DEN-2, serotype DEN-3, and serotype DEN-4. As used herein the term treating or treatment includes prevention; delay in onset; diminution, eradication, or delay in exacerbation of signs or symptoms after onset; and prevention of relapse.

The methods described herein are useful for both prophylactic and therapeutic treatment of *Flavivirus* infections. For prophylactic use, a therapeutically effective amount of the compounds described herein are administered to a subject prior to exposure (e.g., before or when traveling to a location where *Flavivirus* infections are possible), during a period of potential exposure to *Flavivirus* infections, or after a period of potential exposure to *Flavivirus* infections. Prophylactic administration can occur for several days to weeks prior to potential exposure, during a period of potential exposure, and for a period of time, e.g., several days to weeks, after potential exposure. Therapeutic treatment involves administering to a subject a therapeutically effective amount of the compounds described herein after a *Flavivirus* infection is diagnosed.

Administration of compounds described herein or pharmaceutically acceptable salts or prodrugs thereof can be carried out using therapeutically effective amounts of the compounds described herein or pharmaceutically acceptable salts or prodrugs thereof for periods of time effective to treat *Flavivirus* infections. The effective amount of the compounds described herein or pharmaceutically acceptable salts or prodrugs thereof may be determined by one of ordinary skill in the art, and includes exemplary dosage amounts for a mammal of from about 0.05 to about 100 mg/kg of body weight of active compound per day, which may be administered in a single dose or in the form of individual divided doses, such as from 1 to 4 times per day. Alternatively, the dosage amount can be from about 0.05 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In the methods described herein, a *Flavivirus* infection, for example, can be further treated with one or more additional agents. The one or more additional agents and the compounds described herein or a pharmaceutically acceptable salt or prodrug thereof can be administered in any order, including simultaneous administration, as well as temporally spaced order of up to several days apart. The methods may also include more than a single administration of the one or more additional agents and/or the compounds described herein or a pharmaceutically acceptable salt or prodrug thereof. The administration of the one or more additional agent and the compounds described herein or a pharmaceutically acceptable salt or prodrug thereof may be by the same or different routes and concurrently or sequentially.

The compounds described above for use in methods of treating *Flavivirus* infections can also be used in creating medications for use in treating *Flavivirus* infections. Many such medications, including those made in combination with additional agents are described above. For example, any of Compound I, Compound II, Compound III or pharmaceutically acceptable salts or prodrugs thereof as described above can be used to create medications for use in treating a *Flavivirus* infection.

The examples below are intended to further illustrate certain aspects of the methods and compounds described herein, and are not intended to limit the scope of the claims.

Example 1

High Throughput Screening

High throughput screening was performed at Harvard Medical School National Screening Facility-ICCB, Longwood (Boston, Mass.) using the compound libraries named NINDS Bioactives, Chemdiv 2, Maybridge 3, ICBG fungal extracts, Enamine 1, IF lab 1, and Bionet 2.

Expression of WNV in *E. coli* and Purification

Procedures for expression and purification of WNV (EG101 strain) were similar to those described elsewhere by Mueller et al., Int. J. Biochem. Cell. Biol., 39: 606-14 (2007). Briefly, *E. coli* Top10 F' cells (Invitrogen, Carlsbad, Calif.) were transformed with the protease expression plasmid. Cells were grown at 37'C until the $OD_{600}$ was ~0.5. Cells were then induced with isopropyl-1-thio-β-D-galactopyranoside (American Bioanalytical, Natick, Mass.) (0.5 mM), and incubated for 4 h at 37° C. Cells were harvested by centrifugation (5000×g) for 15 min at 4° C., washed once with a buffer containing 50 mM Tris-HCl, pH 7.5, and 200 mM NaCl, centrifuged at 5000×g for 15 min at 4° C., and stored at −80° C. until used.

Proteases were purified by suspending bacterial pellets in 50 mM Hepes, pH 7.0, 500 mM NaCl, (buffer A) with 0.05 mg/ml lysozyme. Cells were incubated for 30 min on ice after addition of 10% stock solution of Triton X-100 (final concentration of 0.5%). Cells were disrupted by sonication for 2 min and the soluble fraction was collected after centrifugation (15,000×g) for 30 min at 4° C. The soluble fraction was incubated for 1 h at 4° C. with Talon resin (BD Bioscience, San Jose, Calif.) which was pre-equilibrated in buffer A. The affinity resin was centrifuged at (400×g) for 10 min at 4° C., washed three times with buffer A, and packed into a column. Washing of the column was continued with the buffer A containing 10 mM imidazole, followed by elution of the protease with buffer A containing 150 mM imidazole. The protease was concentrated and further purified by Sephadex G-75 gel filtration chromatography. The purified protease fractions were pooled and dialyzed against a buffer containing 50 mM Tris-HCl pH 7.5 and 300 mM NaCl (4×1 L). Aliquots (100 μl) were frozen at −80° C.

High Throughput Screen (HTS) Protease Assay

The protease assay (100 μl) described by Mueller et al., Int. J. Biochem. Cell. Biol. 39: 606-14 (2007) was adapted for a 384-well plate format (30.1 μl). Microtiter plates were loaded sequentially with 14 μl of the reaction buffer containing 200 mM Tris-HCl, pH 9.5, and 30% glycerol (TG buffer) using an automated Wellmate (Matrix, Hudson, N.H.) and 6 μl of WNV protease (0.05 μM) (as prepared above) in TG buffer containing 15 mM NaCl (3 mM final concentration). Plates were then centrifuged at 1000×g for 3 min at room temperature to mix samples and pool liquids at the bottom of the wells Inhibitor compounds (100 nl of 5 mg/ml in dimethyl sulfoxide; DMSO) were added to each well in duplicate by a pin-transfer mechanism of a robotic delivery system. The final inhibitor concentrations in the assays varied due to different molecular weights of the compounds from the libraries that were screened. Plates were incubated at room temperature to allow for formation of protease/inhibitor complexes. The fluorogenic substrate, t-butyl-oxycarbonyl(Boc)-Gly-Lys-Arg-7-amino-4-methyl coumarin (AMC) (10 μl in TG buffer; 50 μM final concentration in the reaction mixture), was added using the Wellmate, and the plates were centrifuged for 3 min at 1000×g and incubated at room temperature for 15 min. Fluorescence was measured at excitation and emission wavelengths of 385 nm and 465 nm, respectively, on a Perkin-Elmer (Waltham, Mass.) spectrofluorometer. To validate the assay conditions, aprotinin (bovine pancreatic trypsin inhibitor, BPTI) was used as a positive control. Assay mixtures containing DMSO were used as negative controls. The average of fluorescence values in duplicate wells for a given compound was used to determine the percent activity by taking the values obtained with DMSO controls as 100%. Compounds 1-11, 18-32, and 37-101 above were identified. These compounds reduced the protease activity by ≥50%. The specific reduction in protease activities for these 91 compounds is shown in Table 1. Compounds 12-17 are compounds related to those identified in the HTS screen that also show significant WNV protease inhibition, i.e., >95%.

Example 2

Additional Compounds

Compounds 33, 34, 35, and 36, examples of Compound III, were tested for replicon inhibition and cytotoxicity to WNV and DENV-BKH.

Cell Culture

Baby Hamster Kidney (BHK) and African green monkey kidney epithelial cells (Vero) were cultured in Dulbecco's Modified Eagle Medium (DMEM) (Cellgro®; Mediatech, Inc., Manassas, Va.) supplemented with 10% fetal bovine serum, MEM nonessential amino acid (Cellgro®) (5 ml/liter), and Penicillin-Streptomycin (2.5 ml/liter). Dengue 2 replicon expressing BHK cells and WNV replicon expressing Vero cells were cultured in DMEM as described above containing additionally Geneticin or G418 (Fisher Scientific®, Pittsburgh, Pa.) to maintain the selective pressure of the replicon expressing cells.

Replicon Inhibition Assay

Dengue 2 replicon expressing BHK cells and WNV replicon expressing Vero cells were plated 100 μl into a black 96 well plate (Greiner Bio-One; Monroe, N.C.) with $10^5$ cells/ml concentrations. After 6 hours of incubation, 1 μl of each compound diluted in DMSO to 2.5 mM was added into each well to obtain a 25 μM as the final concentration. Cells were incubated at 37° C. in a humidified $CO_2$ (5%) chamber for 24 hours. The media was then removed and the cells are washed with PBS before adding 20 μl of lysis buffer to each well. A *Renilla* luciferase assay was performed with the addition of 50 μl substrate (Promega Corporation; Madison, Wis.) with a 2 second delay and a 10 second measurement in a Centro LB 960 plate luminescence plate reader (Berthold Technologies; Oak Ridge, Tenn.). The data was analyzed and plotted with GraphPad Prism 5 (GraphPad Software, Inc.; La Jolla, Calif.).

In WNV expressing Vero cells, three compounds were found to be inhibitory for WNV replicon expressing Vero (Compound 33, Compound 34, and Compound 35) (see FIG. 1), and these compounds were analyzed further in varying concentration in order to calculate EC50. Specifically, the cells were prepared as above and the concentration of the compounds were varied (see Table 2). *Renilla* luciferase activity was measured as described above 24 hours after the addition of the compounds.

Figure 2:
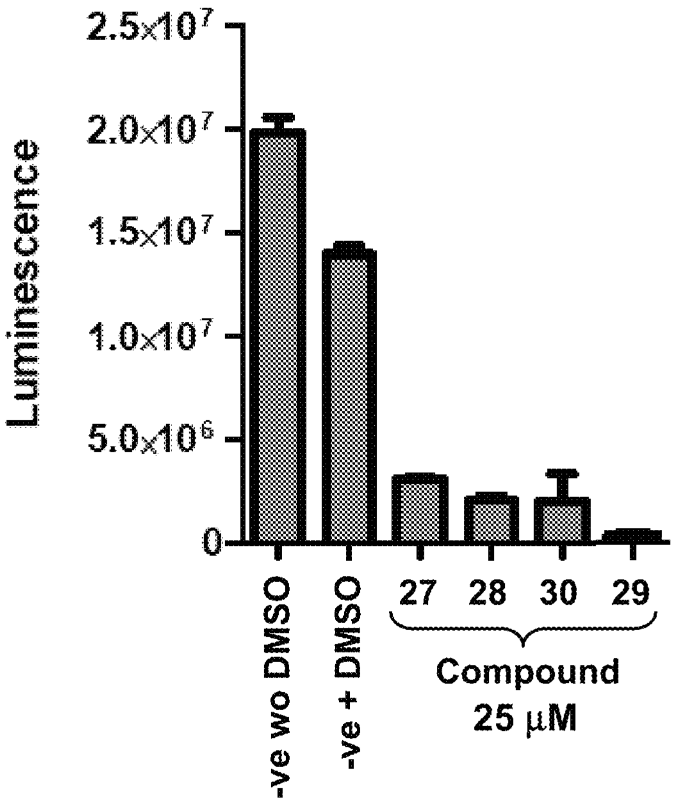
FIG. 2 is a bar graph showing DENV2 BHK replicon inhibition assay results.

In DENV2 BHK cells, four positive compounds from the screen were found to be inhibitory for DENV2 in BHK cells (Compound 33, Compound 34, Compound 35, and Compound 36) (see FIG. 2), and these compounds were analyzed further as above in order to calculate EC50 (see Table 3). *Renilla* luciferase activity was measured as described above 24 hours after the addition of the compounds. EC50 values were also determined for Compound 13 (−7.5 μM), Compound 16 (−4.5 μM), and Compound 17 (~8.3 μM).

Cytotoxicity Assay

Naïve Vero cells were cultured in the presence of varying concentrations of the Compound 33, Compound 34, and Compound 35 to calculate CC50 values. In the same way, Compound 33, Compound 34, Compound 35, and Compound 36 were tested in BHK cells. Naïve BHK and Vero cells were prepared in 96-well plates as described above at various final concentrations. After 18 hours of incubation, 10 μl of MTT reagent (Chemicon; Temecula, Calif.) is added into each well. The cells were incubated for 2 hours before adding 100 μl of detergent and were read in a spectrophotometer as described in the manufacturer's protocol. See Tables 2 and 3 for CC50 values.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

TABLE 1

Reduction In Protease Activity For Compounds Identified In Example 1

| Compound | % Inhibition |
|---|---|
| 1 | 86 |
| 2 | 85 |

TABLE 1-continued

| Reduction In Protease Activity For Compounds Identified In Example 1 | |
|---|---|
| Compound | % Inhibition |
| 3 | 84.5 |
| 4 | 83 |
| 5 | 81 |
| 6 | 76 |
| 7 | 76 |
| 8 | 75 |
| 9 | 74 |
| 10 | 70 |
| 11 | 65 |
| 12 | >95 |
| 13 | >95 |
| 14 | >95 |
| 15 | >95 |
| 16 | >95 |
| 17 | >95 |
| 18 | 83.5 |
| 19 | 76.5 |
| 20 | 76 |
| 21 | 74 |
| 22 | 72.5 |
| 23 | 72 |
| 24 | 70 |
| 25 | 67 |
| 26 | 67 |
| 27 | 66 |
| 28 | 63 |
| 29 | 58 |
| 30 | 53 |
| 31 | 53 |
| 32 | 59 |
| 37 | 71 |
| 38 | 58 |
| 39 | 57 |
| 40 | 56 |
| 41 | 56 |
| 42 | 54 |
| 43 | 54 |
| 44 | 52 |
| 45 | 52 |
| 46 | 50 |
| 47 | 83 |
| 48 | 67 |
| 49 | 58 |
| 50 | 55 |
| 51 | 52 |
| 52 | 52 |
| 53 | 52 |
| 54 | 51 |
| 55 | 51 |
| 56 | 51 |
| 57 | 58 |
| 58 | 55 |
| 59 | 53 |
| 60 | 51 |
| 61 | 51 |
| 62 | 72 |
| 63 | 65 |
| 64 | 65 |
| 65 | 63 |
| 66 | 62 |
| 67 | 61 |
| 68 | 61 |
| 69 | 61 |
| 70 | 60 |
| 71 | 59 |
| 72 | 59 |
| 73 | 58 |
| 74 | 57 |
| 75 | 57 |
| 76 | 57 |
| 77 | 56 |
| 78 | 56 |
| 79 | 56 |
| 80 | 55 |
| 81 | 55 |

TABLE 1-continued

| Reduction In Protease Activity For Compounds Identified In Example 1 | |
|---|---|
| Compound | % Inhibition |
| 82 | 55 |
| 83 | 54 |
| 84 | 54 |
| 85 | 54 |
| 86 | 54 |
| 87 | 54 |
| 88 | 54 |
| 89 | 53 |
| 90 | 52 |
| 91 | 52 |
| 92 | 52 |
| 93 | 52 |
| 94 | 52 |
| 95 | 52 |
| 96 | 51 |
| 97 | 51 |
| 98 | 51 |
| 99 | 50 |
| 100 | 50 |
| 101 | 50 |

TABLE 2

CC50 and EC50 Values for Compounds inhibiting WNV replication in WNV-Vero Cells

| | Compound | | |
|---|---|---|---|
| | 33 | 34 | 35 |
| CC50 | $2.8 \times 10^6$ | 354.7 | 60.94 |
| $R^2$ | 0.4273 | 0.8735 | 0.7924 |
| EC50 | 7.956 | 14.29 | 3.378 |
| $R^2$ | 0.8283 | 0.9893 | 0.9315 |
| TI | 3.52 x 105 | 24.82 | 18.04 |

TABLE 3

Therapeutic Index for Compounds inhibiting DENV replication in DENV-BKH Cells

| | Compound | | | |
|---|---|---|---|---|
| | 33 | 34 | 35 | 36 |
| CC50 | 455638 | 169.9 | 70.07 | 220.1 |
| $R^2$ | 0.7892 | 0.9074 | 0.9167 | 0.7510 |
| EC50 | 10.63 | 34.99 | 2.347 | 63.12 |
| $R^2$ | 0.5634 | 0.9506 | 0.9723 | 0.7809 |
| TI | 42863.4 | 4.8557 | 29.8551 | 3.487 |

What is claimed is:

1. A method of treating a *Flavivirus* infection in a subject, comprising administering to the subject a therapeutically effective amount of the compound of the following formula:

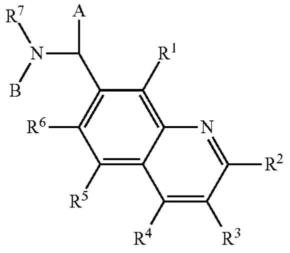

or a pharmaceutically acceptable salt or prodrug thereof, wherein:

$R^1$ is hydroxyl;

$R^2$, $R^3$, $R^4$, $R^5$, and $R^6$ are each independently selected from hydrogen, hydroxyl, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkenyl, substituted or unsubstituted $C_{2-4}$ heteroalkynyl, or halogen;

A is

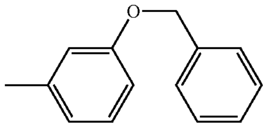

;

B is

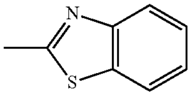

;

and $R^7$ is hydrogen.

2. The method of claim 1, wherein the *Flavivirus* is the West Nile Virus.

3. The method of claim 1, wherein the *Flavivirus* is Dengue Virus serotype DEN-1, Dengue Virus serotype DEN-2, Dengue Virus serotype DEN-3, or Dengue Virus serotype DEN-4.

4. The method of claim 1, wherein the *Flavivirus* is Japanese Encephalitis Virus.

5. A compound of the following formula:

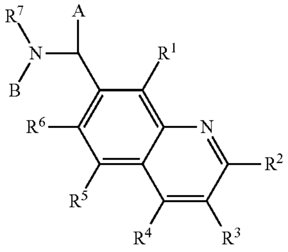

or a pharmaceutically acceptable salt or prodrug thereof, wherein:

$R^1$ is hydroxyl;

$R^2$, $R^3$, $R^4$, $R^5$, and $R^6$ are each independently selected from hydrogen, hydroxyl, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or halogen;

A is

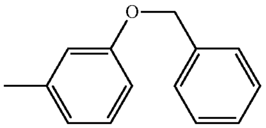

;

B is

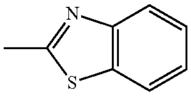

;

and $R^7$ is hydrogen.

6. The compound of claim 5, wherein $R^2$, $R^3$, $R^4$, $R^5$, and $R^6$ are hydrogen.

7. The method of claim 1, wherein $R^2$, $R^3$, $R^4$, $R^5$, and $R^6$ are hydrogen.

* * * * *